United States Patent
Francis

(10) Patent No.: US 6,949,645 B1
(45) Date of Patent: Sep. 27, 2005

(54) PROCESS FOR THE PRODUCTION OF OPIATES

(75) Inventor: Charles A. Francis, Valparaiso, IN (US)

(73) Assignee: Acura Pharmaceuticals, Inc., Palatine, IL (US)

( * ) Notice: Subject to any disclaimer, the term of this patent is extended or adjusted under 35 U.S.C. 154(b) by 0 days.

(21) Appl. No.: 10/849,696

(22) Filed: May 20, 2004

(51) Int. Cl.$^7$ ..................... C07D 489/02; C07D 489/00
(52) U.S. Cl. .......................................... 546/44; 546/43
(58) Field of Search .................................. 546/44, 43

(56) References Cited

U.S. PATENT DOCUMENTS

| | | | |
|---|---|---|---|
| 4,764,615 | A | 8/1988 | Ayyangar et al. |
| 5,981,750 | A | 11/1999 | Corcoran et al. |
| 6,579,985 | B1 | 6/2003 | Hill |

FOREIGN PATENT DOCUMENTS

| | | |
|---|---|---|
| DE | 39887 | 6/1887 |
| DE | 247180 | 5/1912 |
| DE | 418391 | 9/1926 |

OTHER PUBLICATIONS

Brochmann-Hannsen, E. et al., "Biosynthetic conversion of Thebaine to Codeine and Role of Codeine Methyl Ether," *J. Pharm. Sci.*, 1967, vol. 56, pp. 1207-1208.
Carlsen et al., "o-Methylation With Phenyltrimethylammonium Chloride," *Acta Chemica Scandinavica*, 1997, vol. 51, pp. 343-344.
Debska, W. et al, "Determination of Codeine Methyl Ether in Commercial Codeine," *Chem. Anal. (Warsaw)*, 1979, vol. 24, pp. 407-413.
Grimaux, M., "Chime Organique.—Sur La Transformation De La Morphine En Codeine Et An Bases Homologues," *C.R. Acad. Sci.*, 1881, vol. 92, pp. 1140-1143.
Heumann, W., "The Manufacture of Codeine From Morphine," *Bull. Narcotics*, 1958, vol. 3, pp. 15-17.
Hughes, E.D. et al., Influence of Poles and Polar Linkings on the Course Pursued by Elimination Reactions. Part XIII. Decompositions of Some Quaternary Ammonium Salts Containing the Methyl, Benzyl, and Benzhydryl Groups, *J. Chem. Soc. (London)*, 1933, vol. 1, pp. 69-75.
Ikonovski, K, Preparation of Dihydrocodeine by Methylation of Dihydromorphine Obtained From Some By-products in the Manufacture of Opiates, 1982, vol. 32, pp. 241-246.
Ikonovski, K., "Preparation of Codeine by Methylation of Morphine With Phenyltrimethylammonium Methoxide," *Acta, Pharm. Jugoslav*, 1973, vol. 23, pp. 169-171.
Mannich, C., "Ueber Methylderivate des Morphins," *Arch. Pharm.*, 1916, vol. 254, pp. 349-363.
Pfeifer, S., "Über die Verunreinigung von Kodein mit Methylkodein," *Pharmazie*, 1963, vol. 18, pp. 409-410.
Phillips, M.A., Methylation of Morphine, *Chemist Druggist*, 1965, vol. 183, p. 965.
Proksa, B. et al., "Identification and Determination of By-products of the Codeine Synthesie," *Chem. Zvesti.*, 1983, vol. 37, No. 6, pp. 837-842.
Rodionov, W., "L'importance des Ethers Alcoyliques des Acides Sulfoaromatiquea Pour L'alcoylation des Composes Organiques," (*Bull. Soc. Chim. (France)*), 1926, vol. 4, No. 39, pp. 305-325.
Small, L. et al.,—*Chemistry of the Opium Alkaloids*, 1932, US Gov. Printing Office, p. 175-205.
Von Pechmann, H., *Ueber Diazomethan*, 1894, vol. 27, pp. 1888-1895.
White, P.T. et al., "The Poppy," *National Geographic*, 1985, vol. 167, pp. 142-188.

*Primary Examiner*—Charanjit S. Aulakh
(74) *Attorney, Agent, or Firm*—Morgan Lewis & Bockius LLP

(57) ABSTRACT

A morphine component, e.g., a concentrate of poppy straw, is converted into codeine in high yield and high purity and in a highly controlled manner. The conversion process involves the following steps: (a) providing a solution or suspension of a morphine component in an inert solvent or a mixture of solvents; (b) methylating the resultant solution or suspension with a methylating agent in the presence of an alkaline ingredient; and (c) recovering the resultant codeine as the free base or as a salt.

21 Claims, No Drawings

PROCESS FOR THE PRODUCTION OF OPIATES

FIELD OF THE INVENTION

The invention pertains to an improved process for preparing codeine or thebaine starting from a morphine component.

BACKGROUND OF THE INVENTION

Opiates, the alkaloids derived from opium, have long been used to alleviate pain and suffering in humans. Unfortunately, opiates have also been used as illicit narcotics. The unique ability of these compounds to elicit an analgesia accompanied by euphoria has captured the interest of mankind for more than five thousand years, e.g., see P. T. White, et al., *National Geographic,* 1985, vol. 167, p. 142.

Opium (the dried latex of unripe poppy plant capsules) contains over 40 alkaloids. The chief alkaloid constituent of opium is morphine, which is present in varying amounts of 5 to 24% depending on the opium source. Codeine is the opiate of most interest to the pharmaceutical industry. However, codeine is available from natural sources such as opium and poppy straw only in limited quantities, e.g., 2–4%. Since the demand for codeine far exceeds the available natural supply, there is a continuous search for a synthetic method that is capable of producing codeine of high purity in large amount. The pharmaceutical industry is particularly interested in producing codeine in the most cost effective and environmentally friendly manner possible.

It is known that morphine may be methylated at the phenolic hydroxy end (i.e., position 3) to obtain codeine. However, an undesired second methylation at the free hydroxyl end (i.e., position 6) also occurs, e.g., see S. Pfeifer, *Pharmazie,* 1963, vol. 18, p. 409 and E. Brochmann-Hannsen et al., *J. Pharm. Sci.,* 1967, vol. 56, p. 1207. Another competing reaction at the nitrogen end (i.e., position 17) leads to yet another undesirable product, e.g., see W. Debska et al., *Chem. Anal.* (Warsaw), 1979, vol. 24, p. 407; C. Mannich, *Arch. Pharm.,* 1916, vol. 254, p. 349; and B. Proksa et al., *Chem. Zvesti.,* 1983, vol. 37, no. 6, pp. 837–842.

A variety of methylating agents has been reported in the scientific literature as being capable of converting morphine to codeine, see W. Heumann, *Bull. Narcotics,* 1958, vol. 3, p. 15. The earliest attempt to convert morphine into codeine dates back to 1881 and involved the use of methyl iodide, a commonly used methylating agent (see M. Grimaux, *C. R. Acad. Sci.,* 1881, vol. 92, p. 1140). Alkylating agents such as methyl chloride (see M. A. Phillips, *Chemist Druggist,* 1965, vol. 183, pp. 661 and 4454), dimethyl sulfate (see, M. A Phillips, Ibid. and German Patent 418,391), diazomethane (see H. von Pechmann, *Ber.,* 1894, vol. 27, p. 1888; Ibid. 1895, vol. 28, p. 1624 and other reagents (see German Patent 39,887; and L. Small et al., *Chemistry of the Opium Alkaloids,* 1932, US Gov. Printing Office, p. 175) have also been employed in the past. However, virtually all of these prior art methods are accompanied by an uncontrollable decomposition reaction, thereby rendering them of limited value from a commercial standpoint.

One of the biggest disadvantages of methylation reactions is that the nitrogen of the morphine readily reacts with the methylating agent resulting in quaternary ammonium species. These ammonium compounds undergo further degradation compromising both yield and purity. With the introduction of quaternary ammonium reagents containing methyl groups as methylating agents these problems have been greatly reduced. Phenyltrimethylammonium chloride or a modification of it has become the reagent of choice for the manufacture of codeine from morphine since its launch in 1909, see German Patent 247180. Rodionov (*Bull. Soc. Chim.* (France), 1926, vol. 4, no. 39, p. 305) was the first to use the free quaternary ammonium base in lieu of the corresponding chloride. Use of quaternary ammonium bases in the form of alkoxides was among the improvements made to optimize the methylation process, see C. K. Ingold et al., *J. Chem. Soc.* (London), 1933, vo. 1, p. 69; and K. Ikonovski, *Acta. Pharm. Jugoslav.,* 1973, vol. 23, pp. 169–171; Ibid., 1982, vol. 32, pp. 241–246; and U.S. Pat. No. 6,579,985. More recently, Ayyangar et al. (U.S. Pat. No. 4,764,615) have disclosed a method to prepare codeine using phenyltrimethylammonium chloride in the presence of an alkali metal carbonate. O-Methylation of phenols with phenyltrimethylammonium chloride has also been reported (see Carlsen et al. *Acta Chemica Scandinavica,* 1997, 51, pp. 343–344). A solid-phase synthesis using a polymer-bound methylating agent is a new variation in methylating morphine to codeine (see U.S. Pat. No. 5,981,750).

All of the known synthetic routes employ rigorous conditions (very high temperatures and/or high pressures, strong alkaline media, or hazardous reagents/byproducts) and are regularly plagued by problems such as competing secondary reactions, incomplete alkylation, excessive alkylation and/or low yields. Currently, nearly all of the industrial conversions of morphine to codeine are carried out using quaternary ammonium salts. According to reported procedures employing phenyltrimethylammonium chloride it is imperative that exact stoichiometric quantities of morphine and the methylating agent be used to minimize secondary products. Under industrial conditions, an adverse dimethylated product (6-methylcodeine) is invariably produced. In large-scale productions of codeine, it is customary to use morphine in slight stoichiometric excess over the methylating agent to minimize the formation of the over-methylated product. In these cases, however, the unreacted morphine must be removed at the end of the reaction, resulting in additional capital and production costs.

SUMMARY OF THE INVENTION

In one embodiment, the present invention provides a controlled synthetic route leading to codeine free or substantially free of impurities.

In one embodiment, the present invention includes a process for the preparation of codeine, including the steps of providing a solution or suspension of a morphine component in an inert solvent or a mixture of solvents, methylating the resultant solution or suspension with a methylating agent in the presence of an alkaline ingredient and recovering the resultant codeine as the free base or as a salt.

In another embodiment, the present invention includes a process for the preparation of codeine, which includes the steps of providing a solution or suspension of a morphine component in an inert solvent or a mixture of solvents, methylating the resultant solution or suspension with a methylating agent in the presence of an alkaline ingredient wherein the alkaline ingredient employed comprises an alkali metal phosphate; and recovering the resultant codeine as the free base or as a salt.

1. In yet another embodiment, the present invention includes a process for the preparation of codeine, which includes the steps of providing a solution or suspension of a morphine component in an inert solvent or a mixture of solvents, methylating the resultant solution or suspension with a methylating agent in the presence of an alkaline ingredient wherein the alkaline ingredient is selected from the group consisting of tribasic sodium phosphate, tribasic potassium phosphate, potassium dihydrogen phosphate, potassium hydrogenphosphate, sodium acetate, potassium acetate, sodium fluoride, and potassium fluoride and recovering the resultant codeine as the free base or as a salt

DETAILED DESCRIPTION OF THE INVENTION

With reference to reaction Scheme 1 below, it is believed no previously disclosed process is available to avoid the formation of 6-methylcodeine (11) in the preparation of codeine (111) from morphine (i) especially for industrial application. In addition, once formed the complete removal of 6-methylcodeine from codeine is virtually impossible or impractical as evidenced by its significant presence in practically all commercial sources including the USP reference standards. Also, converting 6-methylcodeine back to codeine is not a viable option since an efficient and selective industrial process is yet to be established.

to complete conversion of morphine to codeine. The capability to direct the reaction so that 6-methylcodeine is not formed is a major contributor to the efficiency of the process, which is reflected in the high yield and purity of the product.

A major byproduct as a result of methylation reactions involving quaternary ammonium reagents is dimethylaniline, which is toxic as well as cumbersome to remove from the main product. An increased cost of waste disposal and elevated environmental concerns are a result of the processes employing such methylating agents. Since the recovery or the removal of unreacted morphine and/or dimethylaniline is mandatory, the corresponding capital cost of the production plant and the cost of carrying out the reaction are high.

Embodiments of the invention disclose a simple isolation procedure that removes the byproduct very effectively. In one embodiment, the process takes advantage of the differences in basicity between dimethylaniline and codeine to enable a preferential precipitation of codeine. As demonstrated in the Examples 1 to 7, when dimethylaniline and codeine are present in reaction mixture, codeine phosphate can be selectively precipitated out of the solution as a white

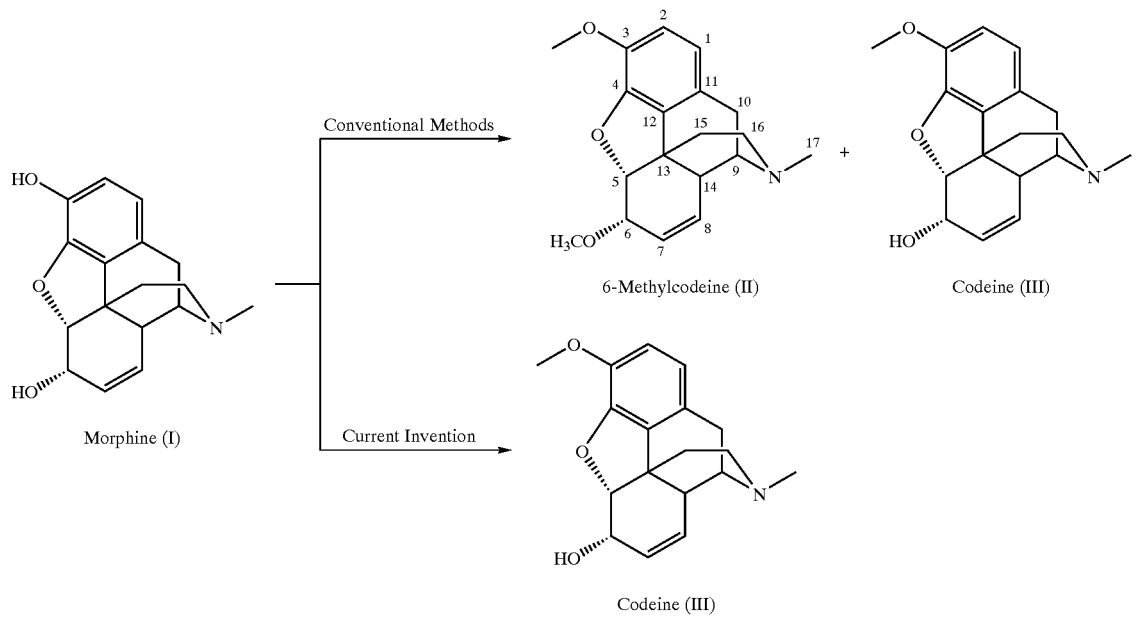

Accordingly, in one aspect the present invention centers on the ability to control a reaction of converting morphine into codeine such that the omnipresent impurity, 6-methylcodeine is not formed or is significantly reduced. Under the disclosed reaction conditions the formation of 6-methylcodeine is not detected, employing analytical test methods with the detection limit of 0.05% w/w (a commonly used limit of detection).

It is believed that the basicity of the reaction medium under the mentioned reaction conditions (hydrogencarbonate salts) is ideal for the formation of the desired product but not the dimethylated impurity. While stronger bases lead to small amounts of 6-methylcodeine, weaker bases do not lead solid while the other component remains dissolved in the solution. A straightforward filtration will ensure the separation of the desired product from the byproduct, while the filtrate may be subjected to a distillation procedure to recover most of the solvent in high purity. In one embodiment, the recycled solvent is suitable for use as reaction solvent in the subsequent production runs.

In yet another embodiment, the process described herein provides for an efficient way of producing codeine or salt thereof, starting from a morphine component.

Embodiments of the present invention prepare codeine in high purity and high yield using the techniques described below. As described in the following paragraphs, embodiments of the present invention can be described as involving: a bicarbonate process, and a phosphate process.

The starting material for carrying out the processes of the invention comprises a "morphine component". For the purposes of this invention, the term "morphine component" shall be understood to encompass morphine itself, a morphine salt or any material, composition, mixture or formulation that contains morphine or a morphine salt such as opium or a concentrate of poppy straw. This term also shall be understood to encompass all phenolic moieties in various opiates and/or opioids. For instance, oripavine, the phenolic analog of thebaine is also included under the term "morphine component." Other examples of suitable starting materials include but are not limited to normorphine, oxymorphone, hydromorphone, dihydromorphine, hydromorphinol, morphine N-oxide, desomorphine, pseudomorphine, nalorphine, naloxone, and naltrexone. From a commercial point of view, the preferred starting material includes a concentrate of poppy straw. Such concentrates typically contain about 50 to about 85 wt. % morphine component on a wet or dry weight basis. In one embodiment, concentrates can contain about 50 to 99 wt. % morphine component on a dry weight basis.

The present invention provides previously unknown methods by which concentrate of poppy straw can be converted to codeine.

Generally, embodiments of the process of the invention include the following steps:
(a) providing a solution or suspension of a morphine component in an inert solvent or a mixture of solvents;
(b) methylating the resultant solution or suspension with a methylating agent in the presence of an alkaline ingredient; and
(c) recovering the resultant codeine as the free base or as a salt.

Embodiments of the invention, including the Bicarbonate and Phosphate Processes are discussed in more detail below.

A. Bicarbonate Process

In one embodiment, suitable examples of the alkaline ingredients employed for the step (b) include but are not limited to alkali metal hydroxides, alkaline earth metal hydroxides, and alkali metal hydrogen carbonates such as sodium hydroxide, potassium hydroxide, magnesium hydroxide, sodium hydrogencarbonate, and potassium hydrogencarbonate. In one embodiment, preferred alkaline ingredients include potassium hydrogencarbonate.

In one embodiment, the present invention includes using a bicarbonate process of the present invention, to convert morphine to codeine using a weak base. In one embodiment, the quantity of alkaline ingredients in step (b) can be in the range of about 0.3 to about 15 grams, dissolved or suspended in a given amount of solvent. In some embodiments, the amount of solvent employed can depend upon the amount of morphine in the morphine component, which is described below. In one embodiment, the concentration of the alkaline ingredient in the solvent can be from about 0.0005 grams per ml. solvent to about 1.0 grams per ml. solvent. In some embodiments, the concentration of alkaline ingredient can be from about 0.0005 grams per ml. solvent to about 0.05 grams per ml. solvent.

In one embodiment, about 15 to about 100 grams of the solvent can be employed per 1 gram of morphine in the morphine component. Suitable examples of the solvent include but are not limited to alcohols, ketones, alkyl halides, aromatic halides, aliphatic ethers, aromatic ethers and aromatic hydrocarbons such as methanol, ethanol, n-butanol, acetone, methylethylketone, cyclohexanone, dichloroethane, chlorobenzene, t-butylmethyl ether, anisole, toluene and xylene or any combination of the mentioned type of solvents (i.e., two or more combined). A preferred solvent includes toluene.

Suitable methylating agents include quaternary ammonium halides and quaternary ammonium alkoxides or salts thereof, including but not limited to such as phenyltrimethylammonium chloride, phenyltrimethylammonium bromide, phenyltrimethylammonium iodide, phenyltrimethylammonium methoxide, and phenyltrimethylammonium ethoxide. The preferred methylating agent comprises phenyltrimethylammonium chloride. Typically the methylating agent is utilized in an amount of about 0.8 to about 2.5 moles per mole of morphine in the morphine component.

In one embodiment, step (b) is carried out at a temperature of about 20 to about 225° C. In another embodiment, step (b) is carried out at a temperature of about 50 to about 150° C. In yet another embodiment, step (b) is carried out at a temperature of about 90 to about 110° C. In one embodiment, the residence time of the reaction is in the range of about 15 minutes to about 72 hours, typically 30 minutes to 28 hours.

After step (b) has been completed, the codeine is recovered from the reaction medium as the free base or as an addition salt such as the phosphate, sulfate, hydrochloride, or acetate. In one embodiment, a process for recovery of the codeine involves separating an alkaline ingredient by filtration, washing the organic layer with an aqueous alkali and water, acidifying an extract of the organic layer with an appropriate acid, filtering the precipitated solid as codeine acid addition salt, and repeatedly washing with hot toluene and ethanol as exemplified in Examples 1 through 3, set forth below. Purification of the isolated material is also described further in Examples 1 through 3.

Alternatively, the isolated codeine salt may be purified by crystallization using an alcohol/water mixture. If desired, the codeine salt may be converted to its free base.

B. Phosphate Process

In certain embodiments of the present invention, suitable examples of the alkaline ingredients employed for the step (b) include but are not limited to alkali metal phosphates (tribasic, dibasic and monobasic), alkali metal acetates, and alkali metal halides such as sodium phosphate, tribasic potassium phosphate, potassium dihydrogen phosphate, potassium hydrogenphosphate, potassium acetate, and potassium fluoride. The preferred alkaline ingredient comprises tribasic potassium phosphate. The conversion of morphine to codeine using such weak bases has not been previously reported.

In one embodiment, the quantity of alkaline ingredients in step (b) can be in the range of about 0.3 to about 15 grams, dissolved or suspended in a given amount of solvent. In some embodiments, the amount of solvent employed can depend upon the amount of morphine in the morphine component. Similar to the above, in one embodiment about 15 to about 100 grams of the solvent can be employed per 1 gram of morphine in the morphine component.

In one embodiment, the concentration of the alkaline ingredient in the solvent can be from about 0.0005 grams per ml. solvent to about 1.0 grams per ml. solvent. In some embodiments, the concentration of alkaline ingredient can be from about 0.0005 grams per ml. solvent to about 0.05 grams per ml. solvent.

Similar to the above, suitable examples of the solvent include but are not limited to alcohols, ketones, alkyl halides, aromatic halides, aliphatic ethers, aromatic ethers and aromatic hydrocarbons such as methanol, ethanol, n-butanol, acetone, methylethylketone, cyclohexanone, dichloroethane, chlorobenzene, t-butylmethyl ether, anisole, toluene and xylene or any combination of the mentioned type of solvents. In one embodiment, a preferred solvent includes toluene or acetone.

Suitable methylating agents include quaternary ammonium halides and quaternary ammonium alkoxides such as phenyltrimethylammonium chloride, phenyltrimethylammonium bromide, phenyltrimethylammonium iodide, phenyltrimethylammonium methoxide, and phenyltrimethylammonium ethoxide. In one embodiment, a preferred methylating agent includes phenyltrimethylammonium chloride. Typically a methylating agent is utilized in an amount of about 0.8 to about 2.5 moles per mole of morphine in the morphine component.

In one embodiment, step (b) is carried out at a temperature of about 20 to about 225° C. In another embodiment, step (b) is carried out at a temperature of about 50 to about 150° C. In yet another embodiment, step (b) is carried out at a temperature of about 90 to about 110° C. In one embodiment, the residence time of the reaction is in the range of about 15 minutes to about 25 hours, typically 30 minutes to 7 hours. The reactions involving tribasic potassium phosphate are fast, often complete in 30–45 minutes. This is another unique attribute of the present invention.

After step (b) has been completed, the codeine is recovered from the reaction medium as the free base or as an addition salt such as the phosphate, sulfate, hydrochloride, or acetate. In one embodiment, the process for recovery of the codeine involves separating alkaline ingredient by filtration, washing the organic layer with an aqueous alkali and water, acidifying an extract of the organic layer with an appropriate acid, filtering the precipitated solid as codeine acid addition salt, and repeatedly washing with hot toluene and ethanol as exemplified in Example 4 set forth below. In one embodiment, purification of the isolated material is described further under Example 4. Alternatively, the isolated codeine salt may be purified by crystallization using an alcohol/water mixture. If desired, the codeine salt may be converted to its free base, also as exemplified in Example 4 set forth below.

A major byproduct as a result of methylation reactions involving quaternary ammonium reagents is dimethylaniline, which is toxic as well as cumbersome to remove from the main product. An increased cost of waste disposal and elevated environmental concerns are an inherent nature of the processes employing such methylating agents. Since the recovery or the removal of unreacted morphine and/or dimethylaniline is mandatory, the corresponding capital cost of the production plant and the cost of carrying out the reaction are high. This invention discloses a simple isolation procedure that removes the byproduct very effectively. In one embodiment, the process takes advantage of the differences in basicity between dimethylaniline and codeine to enable a preferential precipitation of codeine. As demonstrated in the Examples 4 through 7, when dimethylaniline and codeine are present in reaction mixture, codeine phosphate can be selectively precipitated out of the solution as a white solid while the other component remains dissolved in the solution. A straightforward filtration will ensure the separation of the desired product from the byproduct, while the filtrate may be subjected to a distillation procedure to recover most of the solvent in high purity. The recycled solvent is suitable for use as reaction solvent in the subsequent production runs.

Virtually all reported procedures require the use of temperatures greater than 100° C. to bring about the conversion of morphine to codeine (K. Ikonovski, *Acta. Pharm. Jugoslav.*, 1973, vol. 23, pp. 169–171 and W. Heumann, *Bull. Narcotics*, 1958, vol. 3, p. 15). In one embodiment, this invention teaches a process to prepare codeine at 50–60° C. under much milder conditions, in contrast to earlier reports requiring elevated temperatures. This variation also provides for the use of inexpensive solvents such as acetone (as described in Example 6).

The process described herein thus provides for an efficient way of producing codeine or salt thereof, starting from a morphine component.

The following examples are given to illustrate the present invention. It should be understood, however, that the invention is not to be limited to the specific conditions or details described in these examples. Unless otherwise indicated to the contrary, amounts and percentages are on a weight basis. Throughout the specification, any and all references to a publicly available document, including but not limited to a U.S. patent, are specifically incorporated by reference.

EXAMPLE 1

A 1 L three-neck round bottom flask is charged with 9.980 g of morphine alkaloid purified and 500.0 g of toluene. The reaction flask is equipped with a mechanical stirrer, a thermometer, a Dean-Stark trap, a water condenser, an inlet and an outlet for nitrogen. A temperature controller (i2R, Therm-O-Watch brand) coupled with an Aldrich Instatherm oil bath is used to control the reaction temperature. The toluene suspension is stirred mechanically and dried azeotropically at 90–115° C. for 1 hour. The suspension is cooled to 50–60° C., 5.973 g of phenyltrimethylammonium chloride and 131.755 g of potassium hydrogen carbonate are charged. The contents of the flask are stirred mechanically and the suspension is refluxed between 105–115° C. for 28 hours.

The reaction is cooled to room temperature and into this solution is charged 1.000 g of activated carbon (charcoal) and the contents are stirred mechanically at room temperature. The black suspension is filtered using a sintered glass funnel over a bed of diatomaceous earth and the filtrate is collected in a 1-L round bottom flask. The flask containing the filtrate is fitted with a mechanical stirrer and a solution of 3.997 g of 85% phosphoric acid dissolved in 20-g of 95% aqueous ethanol is added dropwise while stirring. A white precipitate is formed which is stirred for 30 minutes at room temperature.

The white precipitate is filtered using a large Buchner funnel. The filter cake is washed with hot toluene (3×30 ml), and 95% aqueous ethanol (3×60 inl) and dried under house vacuum for 18 hours to yield a white solid of codeine phosphate (weight 13.320 g, 99.6% yield). The isolated codeine phosphate is taken in a 250 ml round bottom flask and is charged with 30 g of 10% (w/w) acetic acid and 30 g of water. The resulting solution is mixed with 30 ml of toluene and the two-phase solution is stirred using a magnetic stir bar.

The bi-phasic solution of codeine is charged with 115 ml of 1.0 N sodium hydroxide solution dropwise initially and in portions afterwards. A white precipitate of codeine free base is formed within 30 minutes of stirring in an icebath. The pH of the solution at the end of sodium hydroxide addition is about 11. If codeine is the desired final product the white precipitate may be filtered and dried at this stage to obtain codeine in the form of free base.

The suspension is charged with 120 ml of toluene and stirred, upon which the entire solid dissolved back into the solution. The two-phase solution is taken in a 500 ml separatory funnel and the layers are separated. The aqueous layer is extracted with toluene (3×30 ml) and the extracts are combined, dried over sodium sulfate, filtered, and the filtrate is collected in a 1 L round bottom flask.

With continuous stirring the filtrate is charged with 100 g of denatured ethanol. A previously prepared solution of 3.958 g 85% phosphoric acid in 25 g of 95% aqueous ethanol is added slowly. The container used for the preparation of phosphoric acid solution is rinsed with 95% aqueous ethanol (3×5 g) and the rinses are added to the flask. The formation of codeine phosphate as a white precipitate is observed during the addition of phosphoric acid solution.

The precipitate is filtered using a large Buchner funnel, washed with hot toluene (3×30 ml), 95% aqueous ethanol (2×60 ml), and dried under vacuum oven. The resulting white solid corresponded to a yield of 90% and a purity (by HPLC) of 100% codeine (a/a %), morphine=Not Detected, 6-methylcodeine=Not Detected, α-codeimethine= Not Detected.

EXAMPLE 2

A 1 L three-neck round bottom flask is charged with 9.975 g of morphine alkaloid purified and 500.0 g of toluene. The reaction flask is equipped with a mechanical stirrer, a thermometer, a water condenser, an inlet and an outlet for nitrogen. A temperature controller (i2R, Therm-O-Watch brand) coupled with an Aldrich Instatherm oil bath is used to control the reaction temperature. The toluene suspension is stirred mechanically and refluxed at 90–115° C. for 1 hour. The suspension is cooled to 50–60° C., 6.151 g of phenyltrimethylammonium chloride and 19.850 g of potassium hydrogen carbonate are charged. The contents of the flask are stirred mechanically and the suspension is refluxed between 105–115° C. for 8 hours.

The reaction is cooled to room temperature and into this solution is charged 1 g of activated carbon (charcoal) and the contents are stirred mechanically at room temperature. The black suspension is filtered using a sintered glass funnel over a bed of diatomaceous earth and the filtrate is collected in a 1-L round bottom flask. The flask containing the filtrate is fitted with a mechanical stirrer and a solution of 4.272 g of 85% phosphoric acid dissolved in 20 g of 95% aqueous ethanol is added dropwise while stirring. A white precipitate is formed which is stirred for 30 minutes at room temperature.

The white precipitate is filtered using a large Buchner funnel. The filter cake is washed with hot toluene (3×30 ml), and 95% aqueous ethanol (3×60 ml) and dried under vacuum oven at 30–35° C. for 18 hours to yield a white solid of codeine phosphate (weight 13.333 g, 99.8% yield). The isolated codeine phosphate is purified as stated in Example 1.

EXAMPLE 3

A 500 ml three-neck round-bottom flask is charged with 10.20 g of a concentrate of poppy straw having morphine content of 80.8 wt. %, 425 g of toluene. The reaction flask is equipped with a mechanical stirrer, a thermometer, a Dean-Stark trap, a water condenser, an inlet and an outlet for nitrogen. A temperature controller (i2R, Therm-O-Watch brand) coupled with an Aldrich Instatherm oil bath is used to control the reaction temperature. The toluene suspension is stirred mechanically and dried azeotropically at 90–115° C. for 1 hour. The suspension is cooled to 50–60° C., 6.010 g of phenyltrimethylammonium chloride and 9.720 g of sodium hydrogencarbonate are charged. The contents of the flask are stirred mechanically and the suspension is refluxed between 105–115° C. for 48 hours. The reaction mixture is worked up and purified as stated in Example 1 to obtain codeine free base in a 84% yield.

EXAMPLE 4

A 500 mL three-neck round bottom flask is charged with 5.000 g of morphine alkaloid purified and 250.3 g of toluene. The reaction flask is equipped with a mechanical stirrer, a thermometer, a Dean-Stark trap, a water condenser, an inlet and an outlet for nitrogen. A temperature controller (i2R, Therm-O-Watch brand) coupled with an Aldrich Instatherm oil bath is used to control the reaction temperature. The toluene suspension is stirred mechanically and dried azeotropically at 90–115° C. for 1 hour. The suspension is cooled to 50–60° C., 6.085 g of phenyltrimethylammonium chloride and 35.03 g of tribasic potassium phosphate are charged. The contents of the flask are stirred mechanically and the suspension is refluxed between 105–115° C. for 2.5 hours.

The reaction suspension is cooled to room temperature, filtered, and the filtrate is washed with saturated aqueous sodium chloride (1×60 ml), water (2×60 ml), and 30% aqueous acetic acid solution (4×60 ml). The aqueous layer after the acetic acid washing is concentrated to 100 g and to this solution is charged 0.100 g of activated carbon (charcoal) and the contents are stirred mechanically at room temperature. The black suspension is filtered using a sintered glass funnel over a bed of diatomaceous earth and the filtrate is collected. The filtrate is made alkaline with dilute sodium hydroxide solution to a pH of 12 and the codeine free base is extracted employing isopropyl acetate (3×60 ml). The solvent is evaporated to yield an off-white solid. The solid is taken in a 500 ml round bottom flask fitted with a mechanical stirrer and 35 g of denatured ethanol is added to dissolve the solid. A solution of 1.57 g of 85% phosphoric acid dissolved in 20-g of 95% aqueous ethanol is added dropwise while stirring. A white precipitate is formed which is stirred for 30 minutes at room temperature.

The white precipitate is filtered using a large Buchner funnel. The filter cake is washed with hot toluene (3×30 ml), and 95% aqueous ethanol (3×60 ml) and dried under house vacuum for 18 hours to yield a white solid of codeine phosphate (weight 5.81 g, 87% yield).

EXAMPLE 5

A 500 mL three-neck round bottom flask is charged with 5.002 g of morphine alkaloid purified and 250 g of toluene. The reaction flask is equipped with a mechanical stirrer, a thermometer, a Dean-Stark trap, a water condenser, an inlet and an outlet for nitrogen. A temperature controller (i2R, Therm-O-Watch brand) coupled with an Aldrich Instatherm oil bath is used to control the reaction temperature. The toluene suspension is stirred mechanically and dried azeotropically at 90–115° C. for 1 hour. The suspension is cooled to 50–60° C., 3.187 g of phenyltrimethylammonium chloride and 14.919 g of tribasic potassium phosphate are charged. The contents of the flask are stirred mechanically and the suspension is refluxed between 105–115° C. for 6.5 hours.

The reaction suspension is cooled to room temperature, filtered, and the filtrate is washed with saturated aqueous sodium chloride (1×60 ml), water (2×60 ml), and 30% aqueous acetic acid solution (4×60 ml). The aqueous layer after the acetic acid washing is concentrated to 100 g and to this solution is charged 60 ml of isopropyl acetate. The biphasic solution is made alkaline (to a pH of 14) with aqueous sodium hydroxide. The resulting solution is extracted with isopropyl acetate (3×60 ml), dried organic layer over sodium sulfate, charcoal treated, filtered and the solvent is removed to obtain an off-white solid. This solid is dried under house vacuum for 18 hours to yield a final product of codeine free base (weight 4.070 g, 82% yield).

EXAMPLE 6

A 100 ml three-neck round bottom flask is charged with 1.002 g of morphine alkaloid purified and 30.3 g of acetone. The reaction flask is equipped with a mechanical stirrer, a thermometer, a water condenser, an inlet and an outlet for nitrogen. A temperature controller (i2R, Therm-O-Watch brand) coupled with an Aldrich Instatherm oil bath is used to control the reaction temperature. Powdered tribasic potassium phosphate (4.840 g) and 0.570 g of phenyltrimethylammonium chloride are charged. The contents of the flask are stirred mechanically and the suspension is refluxed between 50–60° C. for 25 hours. The reaction mixture is cooled to room temperature, the insoluble components are filtered, and the filtrate is treated with activated charcoal. The black suspension is filtered using a sintered glass funnel over a bed of diatomaceous earth and the filtrate is collected in a round bottom flask. A solution of 0.410 g of 85% phosphoric acid dissolved in 4.5 g of acetone is added dropwise while stirring. A white precipitate is formed which is stirred for 30 minutes at room temperature. A near quantitative yield of codeine phosphate is isolated. This product may be purified according to the procedure given under Example 1.

EXAMPLE 7

A 500 ml three-neck round-bottom flask is charged with 24.986 g of a concentrate of poppy straw having morphine content of 80.8 wt. %, 507 g of toluene. The reaction flask is equipped with a mechanical stirrer, a thermometer, a Dean-Stark trap, a water condenser, an inlet and an outlet for nitrogen. A temperature controller (i2R, Therm-O-Watch brand) coupled with an Aldrich Instatherm oil bath is used to control the reaction temperature. The toluene suspension is stirred mechanically and dried azeotropically at 90–115° C. for 1 hour. The suspension is cooled to 70° C., 14.620 g of phenyltrimethylammonium chloride and 45.006 g of tribasic potassium phosphate are charged. The contents of the flask are stirred mechanically and the suspension is refluxed between 105–115° C. for 2 hours.

The reaction mixture is cooled to room temperature and into this solution is charged 1.050 g of charcoal and the contents are stirred mechanically at room temperature. The black suspension is filtered using a sintered glass funnel over a bed of diatomaceous earth and the filtrate is collected in a 1-L round bottom flask. The insoluble matter is washed with hot toluene (3×50 g) and denatured ethanol (3×100 g). The flask containing the filtrate is fitted with a mechanical stirrer and a previously prepared solution of 8.929 g of 85% phosphoric acid dissolved in 25-g of 95% aqueous ethanol is added dropwise while stirring. A slight exotherm is observed and care is taken that the temperature of solution did not exceed 30° C. A white precipitate is formed which is stirred for 45 minutes at room temperature.

The white precipitate is filtered using a large Buchner funnel. The filter cake is washed with hot toluene (3×100 g), and hot 95% aqueous ethanol (3×100 g) and dried under house vacuum for 18 hours to yield a white solid of codeine phosphate. The isolated codeine phosphate is taken in a 500 ml Erlenmeyer flask and is charged with 75 ml of water. The resulting solution is mixed with 30 ml of isopropyl acetate and the two-phase solution is stirred using a magnetic stir bar.

The bi-phasic solution of codeine is charged with 136 ml of 1.0 N sodium hydroxide solution dropwise initially and in portions afterwards. A white precipitate of codeine free base is formed within 30 minutes of stirring in an icebath. The pH of the solution at the end of sodium hydroxide addition is about 9. If codeine is the desired final product the white precipitate may be filtered and dried at this stage to obtain codeine in the form of free base.

The suspension is charged with 60 ml of toluene and stirred, upon which the entire solid dissolved back into the solution. The two-phase solution is taken in a 500 ml separatory funnel and the layers are separated. The aqueous layer is extracted with isopropyl acetate (3×45 ml) and the extracts are combined, washed with water (2×25 ml), dried over sodium sulfate, filtered, and the filtrate is collected in a 1 L round bottom flask.

With continuous stirring the filtrate is charged with 60 ml of 95% aqueous ethanol. A previously prepared solution of 7.433 g 85% phosphoric acid in 15 g of 95% aqueous ethanol is added slowly. The container used for the preparation of phosphoric acid solution is rinsed with 95% aqueous ethanol (3×15 g) and the rinses are added to the flask. The formation of codeine phosphate as a white precipitate is observed during the addition of phosphoric acid solution.

The precipitate is filtered using a large Buchner funnel, washed with hot isopropyl acetate (3×30 ml), 95% aqueous ethanol (2×60 ml), and dried under vacuum oven. The resulting white solid corresponded to a yield of 82%.

While the invention has been described in detail and with reference to specific embodiments thereof, it will be apparent to one skilled in the art that various changes and modifications can be made therein without departing from the spirit and scope thereof. Thus, it is intended that the present invention covers the modifications and variations of this invention provided they come within the scope of the appended claims and their equivalents. Further, each and every reference disclosed herein is hereby incorporated by reference.

What is claimed is:

1. The process for the preparation of codeine, which comprises the steps of:
   (a) providing a solution or suspension of a morphine component in an inert solvent or a mixture of solvents;
   (b) methylating the resultant solution or suspension with a methylating agent in the presence of an alkaline ingredient wherein the alkaline ingredient employed comprises an alkali metal phosphate; and
   (c) recovering the resultant codeine as the free base or as a salt.

2. The process according to claim 1, wherein the alkaline ingredient further comprises an alkali metal acetate and an alkali metal halide.

3. A process for the preparation of codeine, which comprises the steps of:
   (a) providing a solution or suspension of a morphine component in an inert solvent or a mixture of solvents;
   (b) methylating the resultant solution or suspension with a methylating agent in the presence of an alkaline ingredient wherein the alkaline ingredient is selected from the group consisting of tribasic sodium phosphate, tribasic potassium phosphate, potassium dihydrogen phosphate, potassium hydrogen phosphate; and (c) recovering the resultant codeine as the free base or as a salt.

4. The process of claim 3 wherein the alkaline ingredient is employed in the amount of about 0.8 to about 50 moles per mole of morphine in the morphine component.

5. The process of claim 3 wherein the methylating agent employed in step (b) is selected from the group consisting of quaternary ammonium halides and quaternary ammonium alkoxides.

6. The process of claim 5 wherein the methylating agent comprises a phenyltrimethylammonium salt.

7. The process of claim 3 wherein the methylating agent is employed in an amount of about 0.8 to about 2.5 moles per mole of morphine in the morphine component.

8. The process of claim 3 wherein the codeine is recovered as the free base or as an acid addition salt.

9. The process of claim 8 wherein the acid addition salt is selected from the group consisting of inorganic and organic acids.

10. The process of claim 8 wherein the acid addition salt is selected from the group consisting of phosphate, hydrochloride, sulfate, acetate, bitartrate, and fumarate.

11. The process of claim 3 wherein the morphine component comprises a concentrate of poppy straw having a morphine content of about 50 to about 99 wt. %.

12. The process of claim 3 wherein the morphine component comprises a concentrate of poppy straw having an oripavine content of about 50 to about 99 wt. %.

13. The process of claim 3 further comprising carrying out step (a) in the presence of a single solvent system selected from the group consisting of an alcohol, a ketone, an alkyl halide, an aromatic halide, an aliphatic ether, an aromatic ether, an aliphatic hydrocarbon, and an aromatic hydrocarbon.

14. The process of claim 3 wherein the single solvent system is selected from the group consisting of methanol, ethanol, n-butanol, acetone, methylethylketone, cyclohexanone, dichloroethane, chlorobenzene, t-butylmethyl ether, anisole, hexane, cyclohexane, toluene and xylene.

15. The process of claim 3 further comprising carrying out step (a) in the presence of a mixed solvent system selected from the group consisting of a mixture of two or more of an alcohol, a ketone, an alkyl halide, an aromatic halide, an aliphatic ether, an aromatic ether, an aliphatic hydrocarbon, and an aromatic hydrocarbon.

16. The process of claim 15 wherein the mixed solvent system is selected from the group consisting of a mixture of methanol and toluene, methanol and xylene.

17. The process of claim 1, wherein the alkali metal phosphate-comprises sodium phosphate.

18. The process of claim 1, wherein the alkali metal phosphate comprises potassium phosphate.

19. The process of claim 18, wherein the potassium phosphate comprises potassium dihydrogen phosphate.

20. The process of claim 18, wherein the potassium phosphate comprises potassium hydrogen phosphate.

21. The process of claim 1, wherein the alkali metal phosphate comprises a tribasic metal phosphatete.

* * * * *